United States Patent [19]

Eilingsfeld et al.

[11] 4,456,672
[45] Jun. 26, 1984

[54] ELECTROPHOTOGRAPHIC RECORDING MATERIALS CONTAINING TRIAZOLE CHARGE CARRIER-TRANSPORTING COMPOUNDS

[75] Inventors: Heinz Eilingsfeld; Karl-Heinz Etzbach, both of Frankenthal; Gerhard Hoffmann, Otterstadt; Peter Neumann, Wiesloch, all of Fed. Rep. of Germany

[73] Assignee: BASF Aktiengesellschaft, Fed. Rep. of Germany

[21] Appl. No.: 489,012

[22] Filed: Apr. 27, 1983

[30] Foreign Application Priority Data

Apr. 29, 1982 [DE] Fed. Rep. of Germany ....... 3215967

[51] Int. Cl.³ .......................... G03G 5/06; G03G 5/14
[52] U.S. Cl. ........................................ 430/59; 430/76; 430/49; 260/157; 548/563
[58] Field of Search .............................. 430/58, 59, 76

[56] References Cited

FOREIGN PATENT DOCUMENTS 2737334 of 0000 Fed. Rep. of Germany .
1522497 of 0000 Fed. Rep. of Germany .
57-82844 5/1982 Japan ...................................... 430/59
57-191646 11/1982 Japan ...................................... 430/58
58-9151 1/1983 Japan ...................................... 430/58
58-9150 1/1983 Japan ...................................... 430/76
247071 1/1960 Netherlands .......................... 430/76

*Primary Examiner*—Roland E. Martin, Jr.
*Attorney, Agent, or Firm*—Keil & Weinkauf

[57] ABSTRACT

Electrophotographic recording materials which comprise an electrically conductive base, charge carrier-producing compounds (sensitizers), and compounds which are charge carrier-transporting when exposed to light, possess high photoconductivity and low conductivity in the dark, and contain, as charge carrier-transporting compounds, 1,2,3-triazoles of the fomula

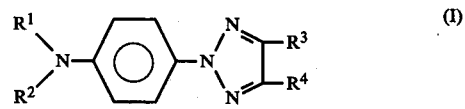

(I)

are used for reprographic purposes and for the production of electrophotographic printing plates, in particular offset printing plates.

4 Claims, No Drawings

ELECTROPHOTOGRAPHIC RECORDING MATERIALS CONTAINING TRIAZOLE CHARGE CARRIER-TRANSPORTING COMPOUNDS

The present invention relates to electrophotographic recording materials which comprise an electrically conductive base, charge carrier-producing compounds, and special charge carrier-transporting compounds.

Electrophotographic processes, materials required for these, and a variety of different structures for recording materials have been disclosed. Advantageous materials for use in the reprography sector are those comprising a polymeric binder which can be adapted to the special requirements of the particular field of use, low molecular weight organic compounds which are soluble, even in relatively high concentrations, in the binder and are capable of transporting charge carriers, and compounds, in particular dyes or pigments, which produce charge carriers when exposed imagewise to actinic light, and are capable of transferring these charge carriers to the charge-transporting compounds, with the aid of the electric field exerted from outside by the electrostatic surface charge. Depending on the field of use of the recording material, these charge carrier-producing compounds can be incorporated, as a separate layer, in a composite structure (cf. German Laid-Open Application DOS No. 2,220,408), or may be present in the form of a monodisperse solution of the dye molecules in a mixture of the binder and the charge carrier-ransporting compounds (cf. German Pat. No. 1,058,836). The multi-layer electrophotographic recording material described in German Laid-Open Application DOS No. 2,220,408 comprises an electrically conductive base, a first layer which is about 0.005–2 μm thick, contains a dye and produces charge carriers when exposed to actinic light, and a second layer which is composed of organic materials which are insulating in the dark and contain one or more charge-transporting compounds.

It has also been disclosed that photosemiconducting organic compounds may be used for the production of electrophotographic printing plates, in particular electrophotographic offset printing plates (cf. German Pat. Nos. 1,117,391 and 1,120,875 and German Published Applications DAS No. 1,522,497 and DAS No. 2,726,116).

The increased demands on reprographic systems necessitate a large variety of recording materials and systems in order that special problems can be solved in an optimum manner. The characteristics desired include high photosensitivity, good resolution and good toning properties. Poor toning, which is frequently objected to and which indicates inadequate differentiation between the field strengths of the exposed and non-exposed areas, is often attributable to the fact that the recording material in the charged state possesses an excessively high conductivity in the dark, so that there is an inadequate surface charge density before imagewise exposure to actinic light.

It is an object of the present invention to provide further electrophotographic recording materials which are suitable, in particular, for the production of electrophotographic printing plates, such as offset printing plates, and which are highly photosensitive and exhibit good resolution and processability and low conductivity in the dark.

We have found that this object is achieved, and that electrophotographic recording materials which comprise an electrically conductive base, charge carrier-producing compounds and charge carrier-transporting compounds and which exhibit the above properties are obtained, if the recording materials contain, as charge carrier-transporting compounds, those of the formula (I)

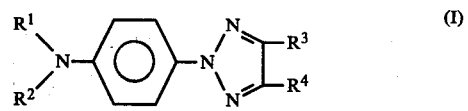

where $R^1$ and $R^2$ are identical or different and are each hydrogen, alkyl, allyl, benzyl or unsubstituted or substituted phenyl, or $R^1$ and $R^2$ together are

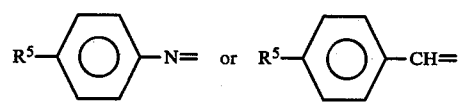

where $R^5$ is $NR^1R^2$, $R^3$ is alkyl or phenyl and $R^4$ is alkyl, vinyl, allyl, carbalkoxy, acryloyl or methacryloyl.

Preferred compounds of this type are those of the formula (I) where $R^1$ and $R^2$ and each alkyl, benzyl or phenyl, $R^3$ is alkyl or phenyl and $R^4$ is alkyl or carbalkoxy. Preferred alkyl radicals are of 1 to 4 carbon atoms, and preferred carbalkoxy radicals are carbomethoxy and carbethoxy.

Examples of very suitable compounds are
(1) 2-(4'-diethylaminophenyl)-4,5-dimethyl-1,2,3-triazole,
(2) 2-(4'-diethylaminophenyl)-4-phenyl-5-carbomethoxy-1,2,3-triazole,
(3) 2-(4'diphenylaminophenyl)-4,5-dimethyl-1,2,3-triazole,
(4) 2-(4'-dibenzylaminophenyl)-4,5-dimethyl-1,2,3-triazole,
(5) 2-(4'-dibenzylaminophenyl)-4-methyl-5-carbomethoxy-1,2,3-triazole,
(6) 2-(4'-dimethylaminophenyl)-4,5-dimethyl-1,2,3-triazole,
(7) 4-diethylamino-4'-(4-methyl-5-carbomethoxy-1,2,3-triazol-2-yl)-benzalaniline and
(8) 4'-diethylamino-4''-(4,5-dimethyl-1,2,3-triazol-2-yl)-azobenzene.

Of these, compounds (1)–(5) have proved particulrly suitable.

The substituted triazoles used according to the invention can be prepared by conventional methods used in organic chemistry.

The charge carrier-transporting compounds used in accordance with the invention can be employed with advantage in both single-layer and multi-layer recording systems on an electrically conductive base.

Suitable single-layer systems have, preferably on a conductive base, a layer of (a) from 45 to 75 parts by weight of a binder, (b) from 30 to 60, in particular from 35 to 50, parts by weight of one of the charge carrier-transporting compounds used according to the invention, (c) if appropriate from 5 to 25 parts by weight of another, essentially inactive binder and (d) from 0.05 to 0.8 part by weight of a compound which produces charge carriers when exposed to actinic light, in particular a suitable dye. Advantageously, an about 5% strength by weight solution in a suitable organic solvent is applied to the clean conductive base so as to give a layer which is about 0.8–40 μm thick after the solvent has been evaporated off in air. The thickness of the layer depends on the intended use, and is, in particular, from 0.8 to 6 μm in the case of electrophotographic printing plates.

Suitable multi-layer systems possess, preferably on an electrically conductive base, for example (a) a charge carrier-producing layer and (b) a charge-transporting layer comprising (b1) from 30 to 60 parts by weight of one or more charge carrier-transporting compounds of the formula (I), and (b2) from 45 to 75 parts by weight of an organic binder, with or without (b3) from 5 to 25 parts by weight of further additives which improve the mechanical properties of the layer. The first layer is advantageously applied to the base in a thickness of from 0.005 to 5, in particular from 0.1 to 0.9 μm, from a solution in a suitable solvent. After this layer has been applied, the second layer is applied so that a layer of from 5 to 25, in particular from 7 to 15, μm thick results after the composite structure has been dried.

In principle, any electrically conductive base can be employed, provided that it is suitable for the field of use of the recording material. Depending on the field of use, preferred bases are aluminum, zinc, magnesium, copper or multimetal sheets, for example crude or pretreated, eg. roughened and/or anodized, aluminum sheets, aluminum foils, polymer films with metallized surfaces, such as polyethylene terephthalate films coated with aluminum by vapor deposition, and special electrically conductive papers. Bases for printing plates are advantageously from 0.08 to about 0.3 mm thick.

The use for which the recording material is intended determines which type of organic binder is suitable for the layers. Examples of suitable binders for the copying sector are cellulose ethers, polyester resins, polyvinyl chlorides, polycarbonates, copolymers, eg. styrene/maleic anhydride or vinyl chloride/maleic anhydride copolymers, or mixtures of these. The choice of binders is governed in particular by their film-forming and electrical properties, their adhesion to the base and their solubility properties. Particularly suitable recording materials for the production of electrophotographic printing plates, especially offset printing plates, are those which are soluble in basic aqueous or alcoholic solvents. These are, in particular, substances possessing groups which make them soluble in alkali, eg. anhydride, carboxyl, sulfonic acid, phenol or sulfonimide groups. Preferred binders are those which in particular have a high acid number, and are readily soluble in basic aqueous-alcoholic solvent systems and have a mean weight average molecular weight of from 800 to 50,000, in particular from 1,500 to 10,000. Thus, we have found that styrene/maleic anhydride/acrylic or methacrylic acid copolymers which contain from 15 to 50% by weight of maleic anhydride units and not more than 35, in particular from 10 to 30, % by weight of acrylic or methacrylic acid units give satisfactory electrophotographic layers having adequate conductivity in the dark. They are highly soluble in washout solutions containing 75% by weight of water, 23% by weight of isobutanol and 2% by weight of sodium carbonate, but are insoluble in fountain solutions conventionally used for offset plates.

Examples of suitable charge carrier-producing compounds or sensitizers for single-layer systems, as also used for the production of electrophotographic printing plates, are triarylmethane dyes, xanthene dyes and cyanine dyes. Very good results were obtained when the compounds according to the invention, of the formula I, were used together with rhodamine B (C.I. 45170), rhodamine 6 G (C.I. 45160), malachite green (C.I. Basic Green 4, C.I. 4200), methyl violet (C.I. 42535) or crystal violet (C.I. 42555). In multi-layer systems, the dye or the pigment is present in a separate charge carrier-producing layer. In this case, azo dyes, phthalocyanines, isoindoline dyes and perylenetetracarboxylic acid derivatives are particularly effective. Good results are achieved with perylene-3,4:9,10-tetracarboxylic acid diimide derivatives, as described in German Laid-Open Applications DOS No. 3,110,954 and DOS No. 3,110,960.

Depending on the use to which it is put, the electrophotographic recording material according to the invention can contain conventional additives, for example flow improvers and plasticizers in the photoconductive layer, or adhesive layers between the base and the layer.

The novel electrophotographic recording materials have a combination of very good properties, in particular high photoconductivity coupled with very low conductivity in the dark, and are hence very useful for the copying sector. They possess substantial advantages when used for the production of electrophotographic printing plates, satisfying high requirements in respect of resolution and length of run.

Although it was known that heterocyclic derivatives, such as oxadiazole derivatives (cf. German Pat. No. 1,058,836), oxazole derivatives (cf. German Pat. No. 1,120,875) or 2,5-bis-(4'-dialkylaminophenyl)-1,3,4-triazoles (cf. German Published Application DAS No. 1,060,260), could be used as charge carrier-transporting compounds, the combination of advantageous properties achieved with the triazoles used according to the invention certainly could not be foreseen. Although German Laid-Open Application DOS No. 2,737,334 describes the use of benzotriazole, together with a binder, a reducible metal compound and a reducing agent for this compound, in an electrically conductive mass for an image recording element which can be developed by heat, this publication does not suggest the results of the present invention.

The Examples which follow illustrate the invention, parts and percentages being by weight.

The measured xerographic values A to D given in the Examples were determined as follows:

The layers were charged uniformly to a surface potential of 600 volts by means of a corona at a direct current voltage of −7.5 kV at a distance of 1 cm, and were then exposed to white light fom a xenon lamp with a luminous intensity of about 0.85 mW.cm$^{-2}$. The following measurements were carried out:

A: Time, in milliseconds (ms), during which the surface potential present before exposure falls to half its value (300 V) on exposure to actinic light.
B: Decrease in potential, in volt (V), which occurs in the same time in the dark as a result of the conductivity of the layers.
C: Surface potential, in volt (V), reached after a charging time of 20 seconds.
D: Decrease in potential in %, based on measured value C, which occurs in the dark in the course of 20 seconds.

EXAMPLES 1 TO 5

A layer comprising 60 parts of a chlorinated perylene-3,4:9,10-tetracarboxylic acid diimide bis-benzimidazole with a chlorine content of about 38% and 50 parts of a copolymer of vinyl chloride, acrylic acid and a maleic acid diester was applied, as a charge carrier-producing layer, in a thickness of about 0.55 μm, to a polyethylene terephthalate film provided, by vapor deposition, with a conductive aluminum layer of about 300 Å thickness.

A charge-transporting layer comprising 45 parts of a commercial polycarbonate binder having a melting range of from 220° to 230° C., 10 parts of a polyester having an acid number of about 40 and a molecular weight of about 4,500 and 40 parts of one of the triazoles listed below under (1) to (5) was applied, from a solution in ethyl acetate, to the above charge carrier-producing layer, the solvent was evaporated off in the air and drying was carried out for 30 minutes at 80° C., the resulting dry layer being 12 μm thick.

Triazoles used:

(1) 2-(4'-diethylaminophenyl)-4,5-dimethyl-1,2,3-triazole,
(2) 2-(4'-diethylaminophenyl)-4-phenyl-5-carbomethoxy-1,2,3-triazole,
(3) 2-(4'-diphenylaminophenyl)-4,5-dimethyl-1,2,3-triazole,
(4) 2-(4'-dibenzylaminophenyl)-4,5-dimethyl-1,2,3-triazole and
(5) 2-(4'-dibenzylaminophenyl)-4-methyl-5-carbomethoxy-1,2,3-triazole.

TABLE 1

Measured xerographic values for the recording materials of Examples 1 to 5.

| Example | Triazole | A (ms) | B (V) | C (V) |
|---|---|---|---|---|
| 1 | (1) | 320 | 0.25 | 1,500 |
| 2 | (2) | 270 | 0.2 | 1,600 |
| 3 | (3) | 190 | 0.3 | 1,450 |
| 4 | (4) | 290 | 0.1 | 1,250 |
| 5 | (5) | 250 | 0.12 | 1,200 |

As the results show, the novel electrophotographic recording materials possess high photoconductivity and low conductivity in the dark. Thus, for example, the layer of Example 1 exhibits a decrease in potential from 600 to 599.9 volts in the course of about 0.3 second in the dark, while the same layer, when exposed with a high-pressure xenon lamp having a luminous intensity of 0.85 mW.cm$^{-2}$ for the same time, exhibits a decrease in potential from 600 to 300 volts. The recording material can be charged to a maximum of more than 1,000 volts, which is substantially above the surface potentials required in copying machines (about 700 volts), and is hence very useful for the copying sector.

EXAMPLE 6

The procedure described in Examples 1 to 5 was followed, except that the charge-transporting layer was prepared from 55 parts of a copolymer of 80% of styrene with 20% of maleic anhydride, and 45 parts of 2-(4'-dibenzylaminophenyl)-4-methyl-5-carbomethoxy-1,2,3-triazole. Xerographic measurements on the recording material showed, as parameter D, a decrease in potential by 12%, and, as parameter A, a decrease in the potential to half its value in 0.25 second. When this layer was used as a copying film in a conventional copying machine employing a dry toner, a large number of copies of good quality were obtained.

EXAMPLE 7

A solution of 45 parts of 2-(4'-dibenzylaminophenyl)-4-methyl-5-carbomethoxy-1,2,3-triazole, 10 parts of a chlorinated polyvinyl chloride, 50 parts of a copolymer of 55% of styrene, 40% of maleic acid anhydride and 5% of methacrylic acid, and 0.3 part of malachite green (C.I. 42000) was applied to a 100 μm thick aluminum foil which had been mechanically roughened to a depth of about 3 μm with a wire brush. After the solvent had been evaporated off, a 4-5 μm thick photoconductive layer remained. The layer was charged to a surface potential of −400 V by means of a d.c. voltage corona in a manner conventionally used in electrophotography, and was exposed imagewise using a 2 kW-high-pressure xenon lamp for 50 seconds. The resulting electrostatic image of the original was rendered visible by dusting with a resin powder colored with carbon black and was fixed to give a non-smudging electrophotocopy by heating at 150° C. The resulting electrophotocopy corresponded to the original and was stable to alkaline solutions in the image areas.

A lithographic printing plate was obtained from the resulting electrophotocopy by treating the latter with a solution comprising 75% of water, 20% of isopropanol, 4.5% of sodium silicate and 0.5% of sodium carbonate. After it had been washed for a short time with water and inked with a fatty ink, the printing plate could be used for printing.

We claim:

1. An electrophotographic recording material comprising an electrically conductive base, charge carrier-producing compounds and charge carrier-transporting compounds, which contains, as charge carrier-transporting compounds, those of the formula (I)

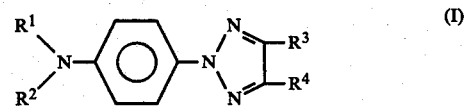

where $R^1$ and $R^2$ are identical or different and are each hydrogen, alkyl, allyl, benzyl or unsubstituted or substituted phenyl, or $R^1$ and $R^2$ together are

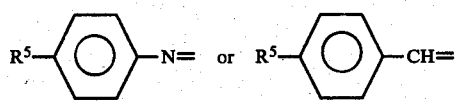

where $R^5$ is $NR^1R^2$, $R^3$ is alkyl or phenyl and $R^4$ is alkyl, vinyl, allyl, carbalkoxy, acryloyl or methacryloyl.

2. An electrophotographic recording material as claimed in claim 1, wherein, in formula (I), $R^1$ and $R^2$ are each alkyl, benzyl or phenyl, $R^3$ is alkyl or phenyl and $R^4$ is alkyl or carbalkoxy.

3. An electrophotographic recording material as claimed in claim 1, comprising an electrically conductive base, a layer containing charge carrier-producing compounds and another layer containing charge carrier-transporting compounds of the formula (I) given in claim 1.

4. An electrophotographic recording material as claimed in claim 1, consisting essentially of an electrically conductive base and a layer containing charge carrier-producing compounds and charge carrier-transporting compounds of the formula (I) given in claim 1.

* * * * *